United States Patent [19]

Cellini et al.

[11] Patent Number: 4,789,741

[45] Date of Patent: Dec. 6, 1988

[54] PROCESS FOR THE SYNTHESIS OF EPSILON-CAPROLACTAM

[75] Inventors: Francesco Cellini, Spinea; Vittorio Gervasutti, Mestre; Raffaele Tancorra, Venezia; Sergio Tonti, Mestre, all of Italy

[73] Assignee: Montedipe S.p.A., Milan, Italy

[21] Appl. No.: 165,234

[22] Filed: Mar. 7, 1988

[30] Foreign Application Priority Data

Mar. 11, 1987 [IT] Italy .................. 19647 A/87

[51] Int. Cl.[4] .......................................... C07D 201/04
[52] U.S. Cl. ................................................ 540/535
[58] Field of Search ....................................... 540/535

[56] References Cited

U.S. PATENT DOCUMENTS 2,716,114  8/1955  Blaser et al. .................. 540/535

Primary Examiner—Robert T. Bond
Attorney, Agent, or Firm—Stevens, Davis, Miller & Mosher

[57] ABSTRACT

The invention concerns a two-step process for the synthesis of caprolactam by reaction of cylcohexanone-oxime with an excess of oleum, carried out in a first step with only a portion of the oxime and in the presence of liquid $SO_2$, according to usual "cold" techniques, the amount of free $SO_3$ in the oleum being equal to or greater than 50% by weight, wherein said "cold" step is completed by a second "hot" step, by adding a second portion of oxime, the ratio between said second portion and said first portion ranging from 0.5 to 1.2.

6 Claims, 4 Drawing Sheets

△-△

PROCESS FOR THE SYNTHESIS OF EPSILON-CAPROLACTAM

BACKGROUND OF THE INVENTION

This invention concerns a process for the synthesis of epsilon-caprolactam, henceforth "caprolactam" and an equipment particularly suited for realizing said synthesis.

In the usual plants caprolactam is obtained by reaction of cyclohexanone-oxime, henceforth "oxime", with an excess of oleum.

According to a first kind of process ("cold" process), the highly exothermal reaction is performed at a very low temperature (about −8° C.), in the presence of liquid sulfur dioxide (which supplies refrigeration by means of evaporation), whereby there is obtained a sulfuric ester of caprolactam, having formula (I):

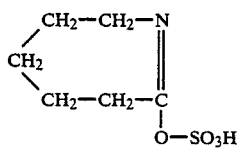

A second kind of process is residing in a "hot" process (in general at 40° C.-150° C.), in the absence of $SO_2$, with the formation of a sulfuric ester of caprolactam, of formula (II):

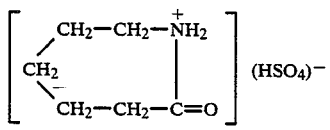

The "cold" processes used so far showed the disadvantage of requiring excessive amounts of liquid $SO_2$ (just for the purposes of refrigeration), but also the "hot" processes are showing drawbacks; if the temperature is very high, about 100° C., the free $SO_2$ content in the oleum must be relatively low (in general below 30% by weight) and the volumes of oleum are thus excessive.

The Applicant has now realized a process, henceforth "cold-hot process" or "mixed process", which allows to limit consistently all these drawbacks and which involves other considerable advantages, specified in more detail further on in the present description.

DISCLOSURE OF THE INVENTION

In its broader aspect, the invention concerns a process for the synthesis of caprolactam by reaction of said oxime with an excess of oleum, the reaction being carried out, at the start, with a first portion only of the oxime to be converted, and in the presence of liquid sulfur dioxide, according to a usual "cold" rearrangement, the amount of free $SO_3$, in the fed-in oleum, being equal to or greater than 50% (but preferably 65%) by weight, characterized in that the initial step of the "cold" reaction is completed by a second "hot" step, by addition of a second portion of oxime, contemporaneously with the evaporation of a greater portion of the residual $SO_2$, the ratio between said second portion and said first portion ranging from 0.5 to 1.2.

Excellent results were obtained by adding to the raw product of the second ("hot") step and in a third (finishing) step, a third portion of oxime, in admixture with a recycle stream, and by subdividing the raw product of said third step into said recycle stream and into a stream of final raw product, which passes on to other usual operative units, the weight ratio between said recycle stream and said third portion of oxime ranging from 10 to 150, the molar ratio between said third portion of oxime and the sulfur dioxide (present at the start of the third step) being equal to or less than 0.3 (but preferably from 0.05 to 0.3) and the weight ratio:

$$\frac{\text{recycle stream} + \text{final raw product}}{\text{third portion of oxime}}$$

being from 10 to 150, but preferably from 40 to 80.

The amount of still uncombined $SO_3$, at the start of the third step, is either equal to or greater than 20%, but preferably from 20% to 26% by weight (averagely 25%).

According to a preferred embodiment of the invention, said third portion of oxime is added to said recycle stream (consisting of part of the product of the third step and subjected to a preliminary venting of the released $SO_2$) inside a statical mixer, the turbulence of the liquid (upstream and downstream of the point of injection of the oxime into the mixer) being corresponding to a very high Reynolds number. The desired level of turbulence can be attained, for instance, by providing the pipeline conveying said reaction liquid (upstream and downstream of the injection point) with fixed helical ribs or with other similar devices showing a low pressure drop. A particularly effective device will be described further on.

As the second portion of oxime is admixed with the raw product of the first rearrangement step, the temperature rapidly rises (from −8° C. to about 0° C.) and continuously increases because of the reaction heat, until attaining a temperature ranging, depending on the heat stabilization system, from 40° to 150° C. (in general from 50° to 100° C.).

The process according to the invention allows to reduce the consumption of oleum as well as the amounts of ammonium sulfate that are formed, as a by-product, after the treatment with ammonia of the sulfuric ester of the lactam. Said process allows, moreover, the maximum possible homogenization of the reaction mixture and to thereby avoid the formation of the so-called hot-spots, where an excessive level of exothermicity may lead to the formation of undesired products. A further advantage is that of conciliating, in the most balanced possible way, two requirements sofar considered quite contrasting with each other, the first being a very high velocity of the reaction mixture, corresponding to a minimum residence time and to a minimum size of the equipment, whereby the Reynolds number increases and the level of homogenization of the mixture increases too.

The second and contrasting requirement is that of reducing to a minimum the pressure drop in the mixer of the third step, which is playing a critical and determining role in the design and in the operation of this kind of plants, deriving from the use of a particular mixer in the third step (as described further on), which is bound to the operative temperature and to the pressure of the ester of caprolactam. In fact, the oxime may be fed into an ester having a temperature lower than the solidification temperature of the oxime itself. The ester may be fed under pressure without thereby incurring undesirable side-reactions in the oxime line, in the case of a stop of the flow (shut-down).

Thanks to the process according to the invention, the consumption of oleum is highly reduced, even in pre-existing plants, by introducing extremely simple changes. The use, in the first step, of concentrated oleum containing for instance 65% by weight of free $SO_3$ (possible only if all the other critical parameters are respected), allows a better and faster catalysis of the oxime rearrangement and there is a useful shrinking of the specific volume of oleum.

Still another result, less striking but nevertheless important, is the possibility of using raw oxime, admixed with only a small percentage of water, without carrying out the usual dangerous dehydrating operations (below 2% $H_2O$, the oxime is heavily unstable). Finally, the homogenization level, in the reaction zone, is excellent while the pressure drop is lowest.

The invention will now be illustrated in some of its aspects by the help of a series of figures which, in no way, shall be taken as limitative of the inventive scope of the invention itself.

Figure 1:
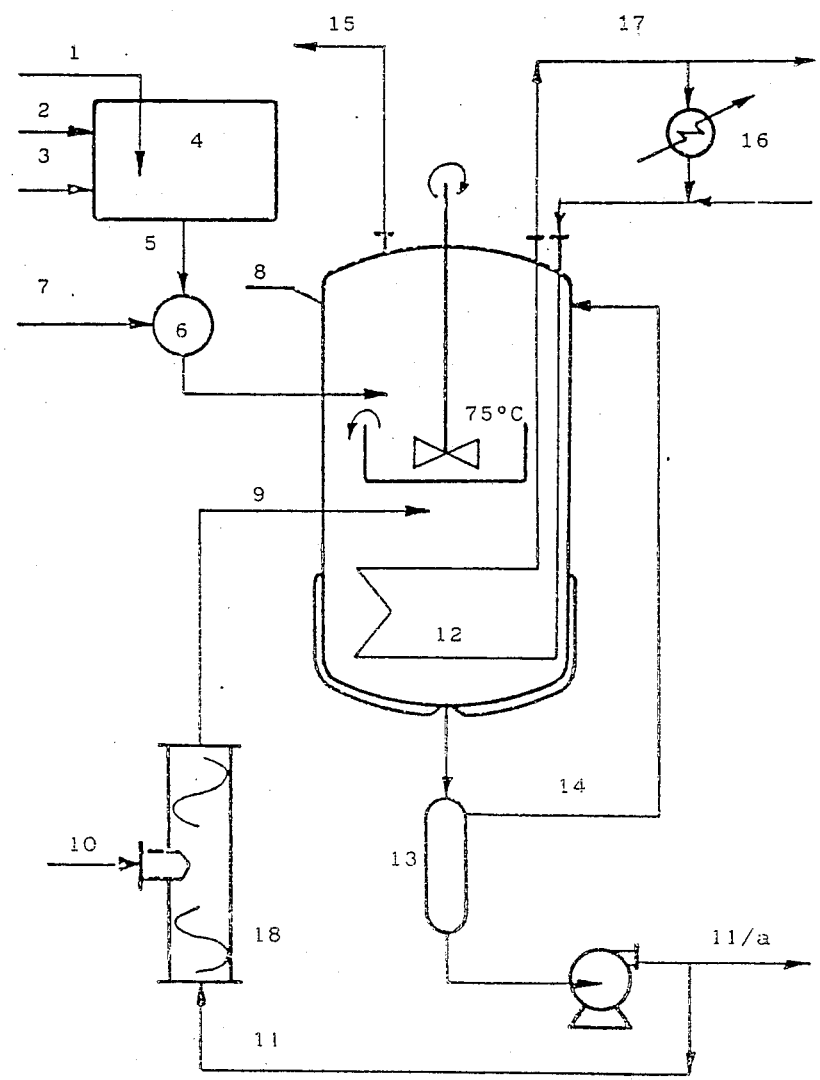
FIG. 1 is a schematical representation of the whole process.

According to FIG. 1, a stream of oxime (1), a stream of oleum (2), in excess with respect to the stoichiometric amount, and a stream of liquid $SO_2$(3) enter the first step of the rearrangement (4), working at a low temperature (about $-8°$ C.) according to a usual technique. The product (5) flowing out of this step is consisting of the sulfuric ester of caprolactam, of free sulfur dioxide (not combined in the form of an ester) and of residual sulfur trioxide.

An additional stream of oxime (7) is fed into a small-size apparatus (6). This reaction mixture enters, thereafter, at a low temperature (about 8° C.), an evaporator-reactor (8), where both the evaporation of the residual $SO_2$ as well as the second rearrangement step, bound to the contact (in the "hot" state) of the $SO_3$ excess with the additional oxime feed are carried out. We are thus in the presence of a multi-step process for the rearrangement of the oxime, the first step being of the "cold" type and the successive steps being of the "hot" type.

The reacting mixture first drops onto a tray (heated by a heating coil not shown in the drawings) where, because of the rearrangement heat (at about 75° C.) the most part of the residual $SO_2$ is released; the same mixture, thereafter, spills over onto the underlying part, preferably containing a series of trays (not indicated on the drawings), where it meets a second mixture (9) obtained by injecting a third portion of oxime (10) into a recycle stream (11).

The heat of the reaction between the oxime and $SO_3$ raises considerably the temperature, which temperature may however be suitably kept at an optimal level (in general 85°–100° C.) by means of a suitable thermal fluid (e.g. ethylene glycol) circulating inside a coil system (12). Once the conversion is completed, the product passes into venting tank (13) where the last traces of $SO_2$ are separated and recycled back to evaporator-reactor (8) through pipeline (14); the vent (15) discharges all the sulfur dioxide released in the whole system. Heat exchanger (16), cooled, for instance, by water, reduces the temperature of thermal fluid (17). The oxime conversion does not occur (or occurs only as a minimum percentage) inside the static mixer (18), whose task is exclusively that of dispersing in the most homogeneous way the oxime inside the recycle stream (11), containing the $SO_3$ required by the rearrangement of the third step.

The non-recycled product (11/$a$) is finally transferred to a neutralization zone and then to a zone for the separation of the ammonium sulfate (see for instance Italian Patent No. 1.144.912 and Italian Patent Publication Nos. 22427 A/82 and 20018 A/84.

Figure 2:
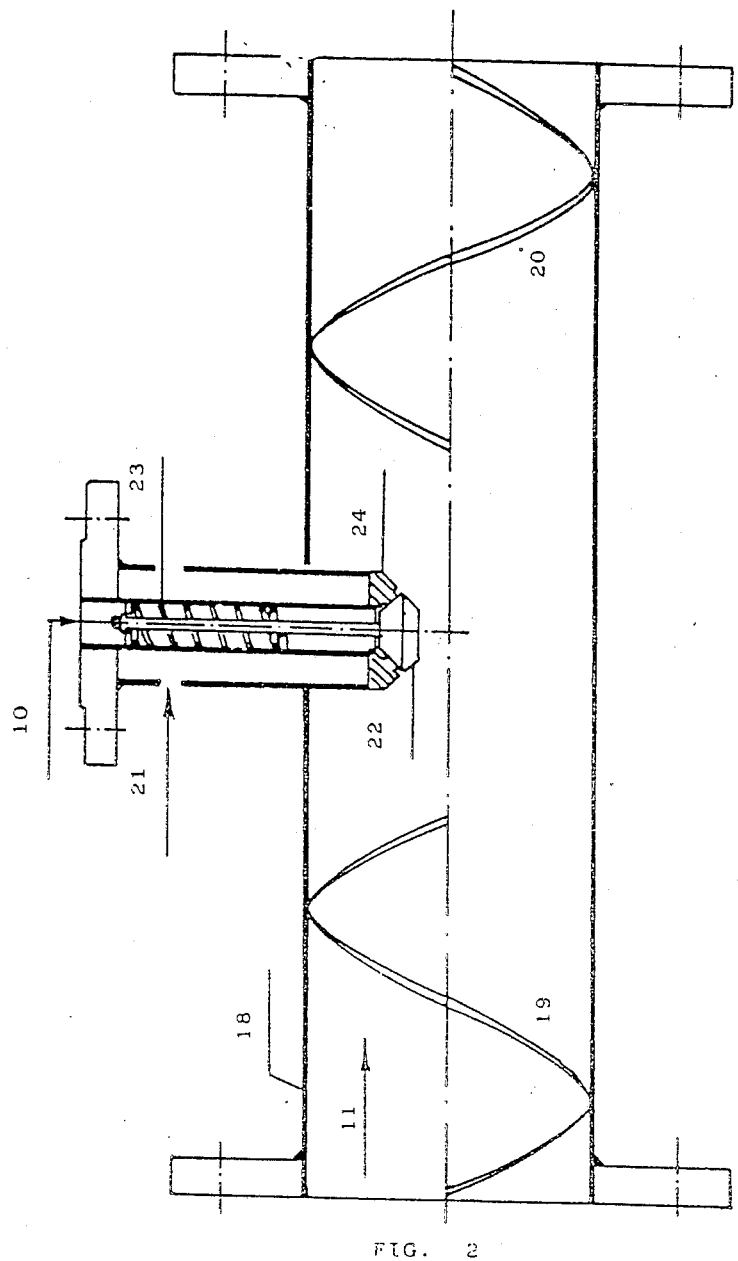
FIGS. 2, 3 and 4 represent some details of the static mixer, lying in the third step of the "mixed process" according to the invention.

According to FIG. 2, the sulfuric recycle stream (11), consisting of sulfuric esters and coming from apparatus (8), enters flanged cylinder (18), whereinto a stream of oxime (10) is injected. Upstream and downstream of the injection point of said cylinder there are arranged two fixed helicoidal fins (19) and (20). The injection nozzle is sheathed by a heating jacket thermostabilized by means of stream (21) or of another equivalent thermal fluid; the oxime inlet is blocked by a sealing organ (22) consisting of a check valve provided with a tapered piston, sliding in an axial sense, recalled by a calibrated spring (23) against a sealing ring (24).

When the difference between the oxime pressure, upstream of the check valve, and the pressure downstream of same valve is greater than a prefixed value (generally 0.5 bar), the gate opens and allows the oxime to flow in. When the pressure drops, the gate is recalled by spring (23), stops the flow and hinders the ester to flow upwards along the oxime duct where a dangerous reaction could occur, with a consistent increase of the temperature and a partial carbonization of oxime. The device is acting both as a thermostated feeding nozzle as well as a typical check valve, which allows to avoid clogging of the feeding duct by carbonaceous residues. This occurrence would be otherwise quite probable, especially in the case of a shut-down or when starting up the whole plant.

Figure 3:
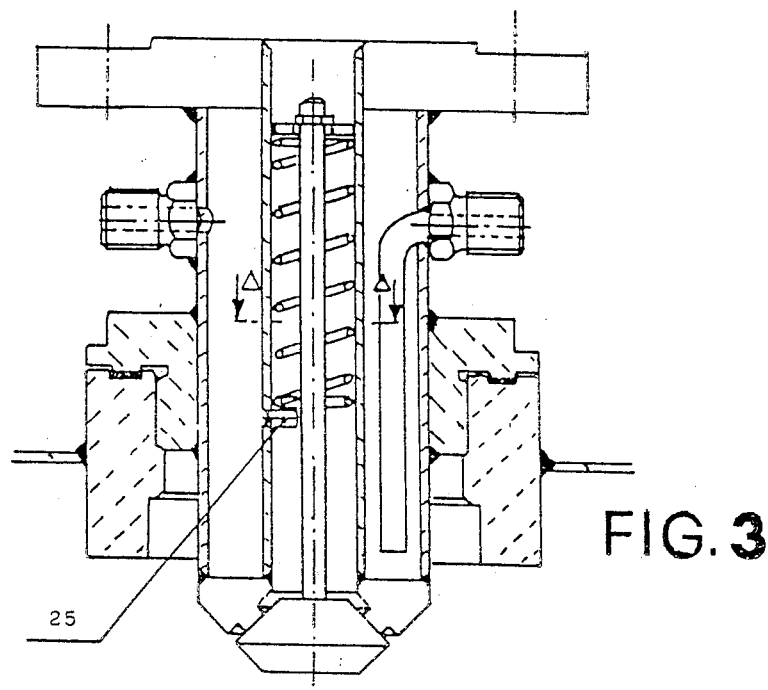
Figure 4:
Figure 5:
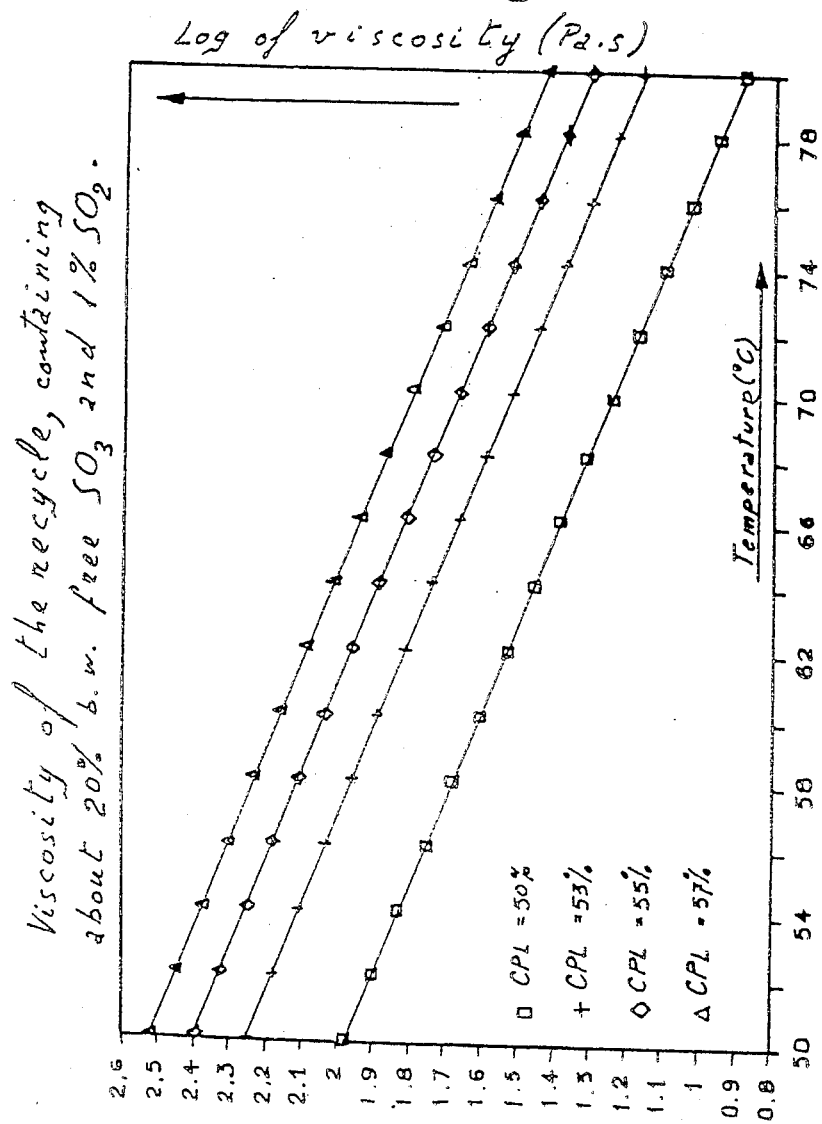
FIG. 5 is a diagram showing the viscosity of the recycle stream which is admixed with the oxime in same third step of the process.

FIGS. 3 and 4 illustrate mechanical details of the structure of the feeding nozzle. In particular stopping pins (25) should be taken into consideration.

The following examples are intended only as an illustration of some aspects of this invention, without, however, limiting in any way the inventive scope of the invention itself.

EXAMPLE 1

(comparative)

According to the first of the given figures, 1333 parts by weight of molten cyclohexanone oxime (1), containing about 2% by weight of water, and 2034 p.b.w. of oleum (2), containing 65% by weight of free $SO_3$, and an amount of liquid $SO_2$ (3) sufficient for the thermal purposes of the synthesis (at about $-8°$ C.) were continuously fed to the first rearrangement step (4).

The effluent from the first step (5) was transferred to apparatus (6) together with a second portion of said oxime (1066 p.b.w.), adjusting the temperature at 0° C. by metering liquid sulfur dioxide. The heat of reaction made the temperature in the reactor-evaporator (8) rise to 75° C. and the greatest part of the sulfur dioxide consequently evaporated. The raw product was then vented into separator tank (13) and conveyed through line (11/$a$) to a neutralization zone (with $NH_3$) and thereupon conveyed to a purification and recovery zone (for pure caprolactam) of the type described in Italian Patent Publication No. 19737 A/87. The final pure lactam showed the following characteristics:

permanganate number (at a 3% b.w. solution):20.000 seconds optical density (290 nanometers) = 0.03 volatile bases (milliequivalents/Kg) = 0.2.

The rearrangement selectivity (with respect to oxime) was greater than 99% and the amount of by-products (ammonium sulfate) was about 1.35 kg per kg of caprolactam. As to the definitions of optical density and of permanganate number, see Italian Patent No. 1098009 and U.S. Pat. No. 3,914,217.

EXAMPLE 2

Example 1 was repeated accumulating the product and continuously recycling to the reactor-evaporator (8) about 15,000 parts by weight of product through lines (11) and (9), together with a third addition of oxime (350 parts b.w.), coming from line (10) and injected into a static mixer (18). After having reached the desired operative temperature in the third step (90° C. in the lower part of the reactor-evaporator, heat-stabilized by means of ethylene glycol), we did separate the product bound to neutralization and to the successive operations (11/a). The final pure caprolactam showed the same physical and chemical features as the lactam of example 1, but the amount of by-products (ammonium sulfate) was lowered down to 1.17 kg/kg. In other words, without the addition of the third step, the amount of by-products would have been greater by more than 13%. Moreover, we must point out that an attempt to add the oxime of the third step (350 parts) together with the oxime of the second step (1066 parts) had previously caused an enormous thermal unbalance, a dangerous rise in viscosity and an unacceptable worsening of the quality of the final product.

From all this it will be appreciated how critical it is to resort to said third reaction step, under conditions of high dilution of the oxime (and at higher temperatures with respect to the second step).

EXAMPLE 3

Example 2 was repeated, bringing the amount of the oxime of the third stage (line 10) up to 600 p.b.w., while maintaining the weight ratio R=recycle stream (line 11)/oxime (line 10) at about 40 and adjusting the steady temperature (in the lower part of the reactor-evaporator) at about 100° C. Pure caprolactam of excellent quality was obtained and the amount of by-products unbelievably dropped down to 1.07 kg per kg of pure caprolactam.

Without such third step addition, as it can easily be calculated, the amount of by-products would have been approximately higher than 21%.

EXAMPLE 4

(comparative)

Example 2 was repeated, replacing the starting concentrated oleum by 2125 parts by weight of a more diluted oleum (45% b.w. of $SO_3$) and reducing the oxime percentage in the third step down to 200 parts by weight. After neutralization and purification, we obtained: a caprolactam of a much poorer quality and a selectivity of the synthesis (with respect to oxime) between 97 and 98%; this test is showing how critical proves to be the use of a much more concentrated oleum in the initial "cold" step.

What is claimed is:

1. A process for the synthesis of caprolactam by reaction of cyclohexanone-oxime with an excess of oleum, achieved in a first step with a first portion of oxime and in the presence of liquid $SO_2$, according to the usual "cold" technique, where the amount of free $SO_3$ in the oleum is equal to or greater than 50% b.w., characterized in that the "cold" step is completed by a second "hot" step, by adding a second portion of oxime, and in that the ratio between said second portion and said first portion of oxime ranges from 0.5 to 1.2.

2. A process according to claim 1, characterized in that to the raw product of the second "hot" step there is added, in a third step, a third portion of oxime, admixed to a recycle stream, and in that the raw product of the third step is subdivided into said recycle stream and into a stream of final raw product, the weight ratio between said recycle stream and said third portion of oxime being from 10 to 150, the molar ratio between said third portion of oxime and the uncombined $SO_3$ present at the start of the third step, being equal to or less than 0.30 (preferably from 0.05 to 0.30) and the weight ratio:

$$\frac{\text{recycle stream + final raw product}}{\text{third portion of oxime}}$$

being ranging from 10 to 150.

3. A process according claim 2, wherein said ratio:

$$\frac{\text{recycle stream + final raw product}}{\text{third portion of oxime}}$$

ranges from 40 to 80.

4. A process according to claim 2, wherein the temperature of the third step is greater than the temperature of said second step.

5. A process according to claim 2, wherein said third portion of oxime is injected into said recycle stream inside a statical mixer, preferably fitted with fixed helicoidal blades (fins or ribs or baffles).

6. A process according to claim 5, characterized in that said third portion of oxime is injected through a thermostated nozzle provided with a check valve.

* * * * *